US012622741B2

(12) United States Patent
Choi

(10) Patent No.: US 12,622,741 B2
(45) Date of Patent: May 12, 2026

(54) CONDUCTIVE ELECTRODE FOR ELECTROSURGICAL HANDPIECE AND MANUFACTURING METHOD THEREFOR

(71) Applicants:In-Sang Choi, Uiwang-si (KR); Eun A. Choi, Anyang-si (KR); Bo Hwan Choi, Seongnam-si (KR)

(72) Inventor: In-Sang Choi, Uiwang-si (KR)

(73) Assignees: In-Sang Choi, Uiwang-si (KR); Eun A. Choi, Anyang-si (KR); Bo Hwan Choi, Seongnam-si (KR)

( * ) Notice: Subject to any disclaimer, the term of this patent is extended or adjusted under 35 U.S.C. 154(b) by 329 days.

(21) Appl. No.: 18/270,607

(22) PCT Filed: Dec. 20, 2021

(86) PCT No.: PCT/KR2021/019366
§ 371 (c)(1),
(2) Date: Jun. 30, 2023

(87) PCT Pub. No.: WO2022/145840
PCT Pub. Date: Jul. 7, 2022

(65) Prior Publication Data
US 2024/0081889 A1     Mar. 14, 2024

(30) Foreign Application Priority Data

Dec. 31, 2020    (KR) ........................ 10-2020-0188948
May 21, 2021    (KR) ........................ 10-2021-0065249

(51) Int. Cl.
A61B 18/12        (2006.01)
A61B 18/14        (2006.01)
*A61B 18/00*        (2006.01)

(52) U.S. Cl.
CPC ...... A61B 18/14 (2013.01); *A61B 2018/0091* (2013.01)

(58) Field of Classification Search
CPC . A61B 18/14; A61B 18/1412; A61B 18/1402; A61B 2018/0013; A61B 2018/00107; A61B 2018/00083
See application file for complete search history.

(56) References Cited

U.S. PATENT DOCUMENTS 5,120,596 A * 6/1992 Yamada .............. C23C 14/0641
428/421
5,637,111 A * 6/1997 Sutcu ................. A61B 18/1445
606/174
(Continued)

FOREIGN PATENT DOCUMENTS

JP        2009-119209 A      6/2009
JP        2019-205921 A     12/2019
(Continued)

OTHER PUBLICATIONS

Korean Office Action issued on Mar. 9, 2021 in counterpart Korean patent application No. 10-2020-0188948 (5 pages in Korean).
(Continued)

*Primary Examiner* — Daniel W Fowler
(74) *Attorney, Agent, or Firm* — NSIP Law

(57) ABSTRACT

The present invention relates to a conductive electrode of a monopolar handpiece, used in an electrosurgical handpiece. Specifically, the purpose of the present invention is to provide a conductive electrode for an electrosurgical handpiece and a manufacturing method therefor, in which during surgery, tissue carbonization and smog production nearly do not occur, and tissues do not adhere to the electrode.

5 Claims, 6 Drawing Sheets

(56)              References Cited

U.S. PATENT DOCUMENTS

| | | | | |
|---|---|---|---|---|
| 6,070,444 | A * | 6/2000 | Lontine | A61B 18/1402 |
| | | | | 72/46 |
| 6,132,427 | A * | 10/2000 | Jones | A61B 18/1402 |
| | | | | 606/41 |
| 7,377,919 | B2 * | 5/2008 | Heim | A61B 18/1402 |
| | | | | 606/41 |
| 8,439,910 | B2 * | 5/2013 | Greep | A61B 18/1402 |
| | | | | 606/45 |
| 2006/0217709 | A1 * | 9/2006 | Couture | A61B 18/1442 |
| | | | | 606/51 |
| 2010/0168745 | A1 * | 7/2010 | Loeser | C22C 47/08 |
| | | | | 606/49 |
| 2012/0010628 | A1 * | 1/2012 | Cooper | A61B 34/30 |
| | | | | 606/130 |
| 2016/0235462 | A1 * | 8/2016 | Canady | A61B 18/042 |
| 2017/0303954 | A1 * | 10/2017 | Ishii | A61B 18/1445 |

FOREIGN PATENT DOCUMENTS

| | | | |
|---|---|---|---|
| JP | 2020-062297 | A | 4/2020 |
| KR | 10-1967349 | B1 | 4/2019 |
| KR | 10-2021266 | B1 | 9/2019 |
| KR | 10-2196406 | B1 | 12/2020 |
| KR | 10-2286804 | B1 | 8/2021 |

OTHER PUBLICATIONS

Korean Office Action issued on Mar. 9, 2021 in counterpart Korean patent application No. 10-2021-0065249 (4 pages in Korean).

* cited by examiner

【FIG. 1】
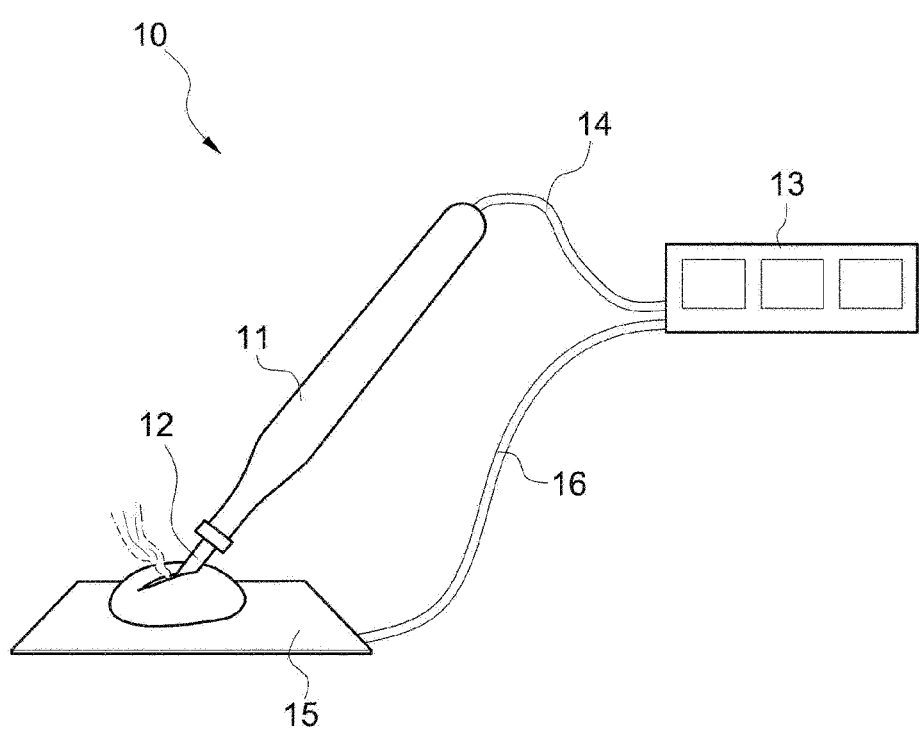

【FIG. 2】
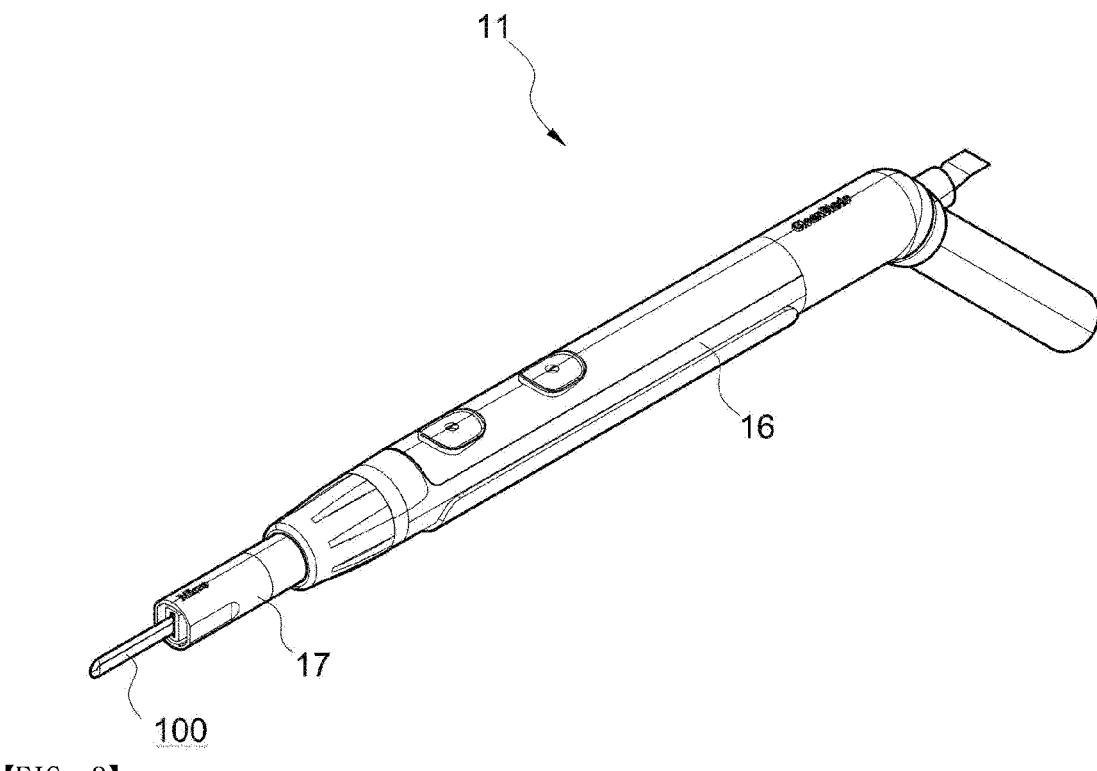
11
16
17
100
【FIG. 3】
50
102
103
101

【FIG. 4】
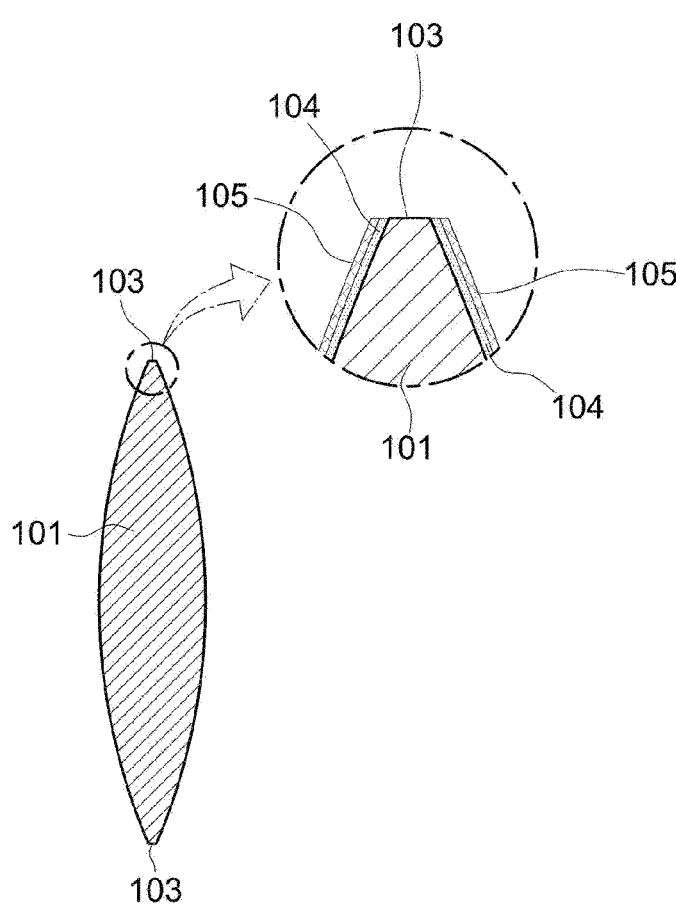

[FIG. 5]
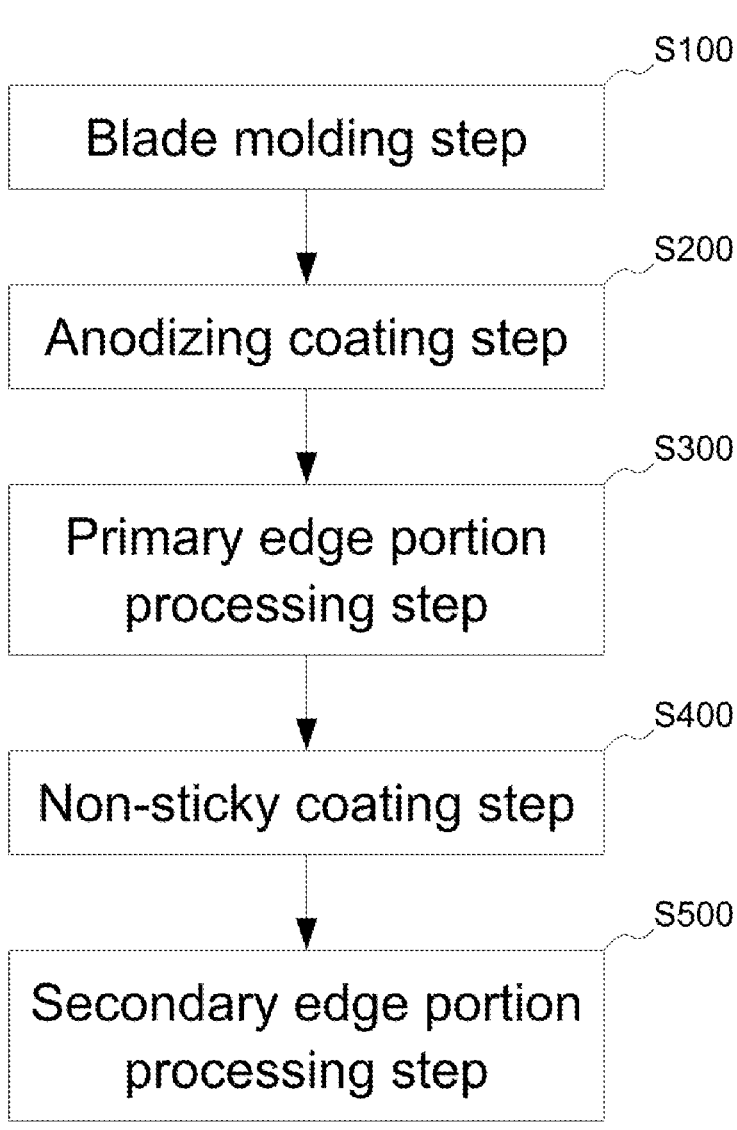

【FIG. 6】
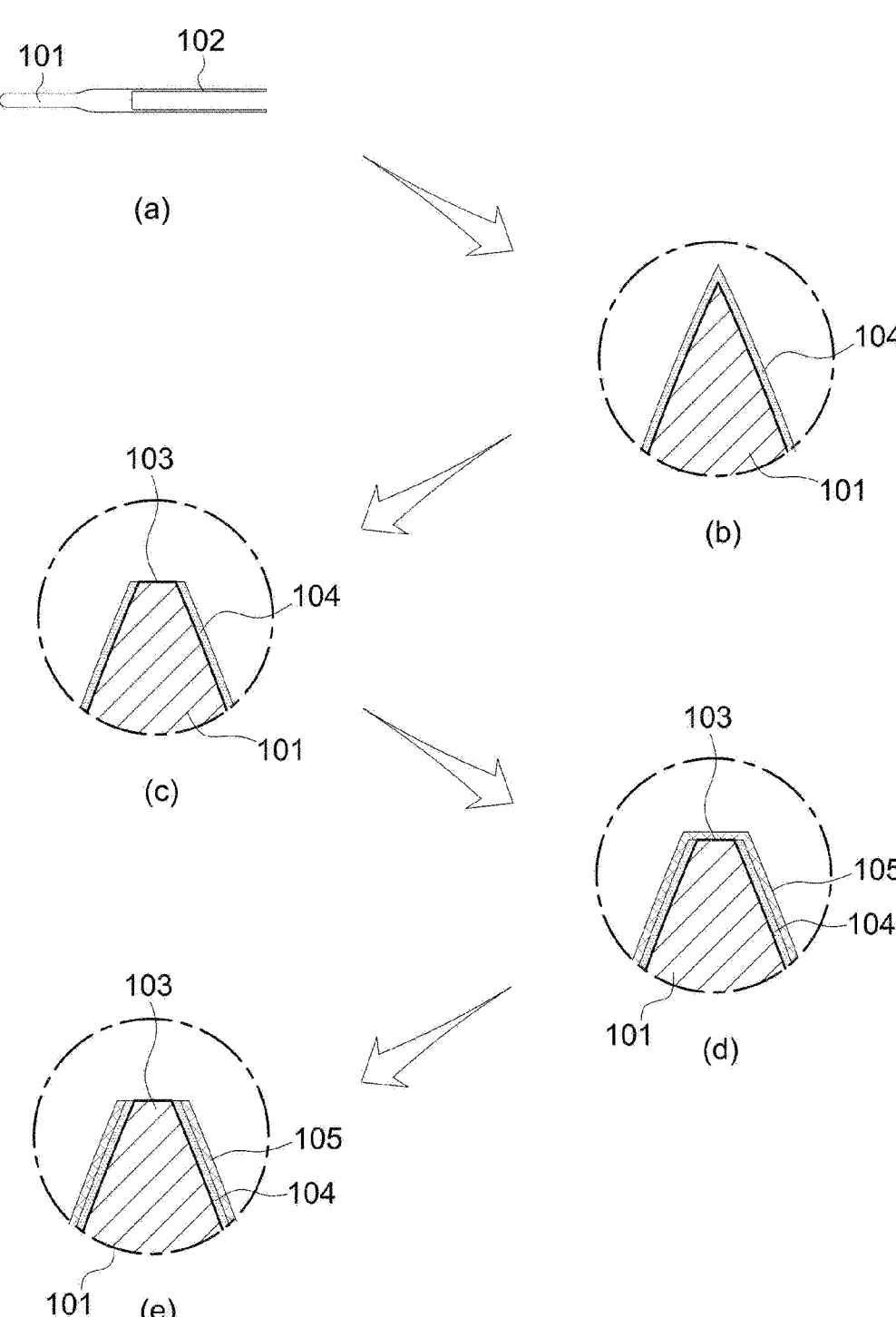

【FIG. 7】
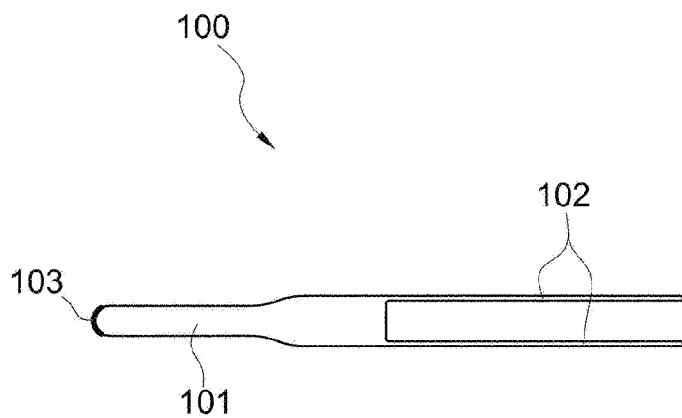
【FIG. 8】
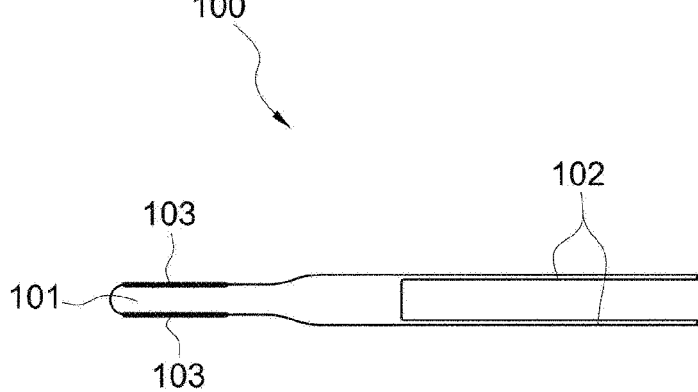

CONDUCTIVE ELECTRODE FOR ELECTROSURGICAL HANDPIECE AND MANUFACTURING METHOD THEREFOR

CROSS REFERENCE TO RELATED APPLICATIONS

This application is a U.S. National Stage Application of International Application No. PCT/KR2021/019366, filed on Dec. 20, 2021, which claims the benefit under 35 USC 119(a) and 365(b) of Korean Patent Application No. 10-2020-0188948, filed on Dec. 31, 2020 and Korean Patent Application No. 10-2021-0065249, filed on May 21, 2021, in the Korean Intellectual Property Office, the entire disclosure of which is incorporated herein by reference for all purposes.

TECHNICAL FIELD

The present disclosure relates to a monopolar handpiece conductive electrode used for an electrosurgical handpiece and, more particularly, an aspect of the present disclosure is to provide an electrosurgical handpiece conductive electrode and a method for manufacturing the same, wherein minimal tissue carbonization and smog occur during surgery, and no tissue adheres to the electrode.

BACKGROUND ART

Conventionally, iron-made surgical scalpels have been used to conduct tissue incision surgeries, and are still widely used today. However, as a result of highly developed modern engineering technologies, cutting-edge surgical tools that use energy such as electricity, laser, or ultrasonic waves have appeared.

The principle of energy-based surgical instruments is as follows: energy is appropriately injected into the tissue of a human body such that the tissue is changed, thereby having a surgical effect.

The most widely used energy-based surgery among them is electrosurgery, which refers to a surgical method in which high-frequency or radio-frequency electric energy is used to incise, excise, or cauterize a patient's tissue.

Human nervous systems react very sensitively to low-frequency electricity of up to 1,000 Hz. Therefore, if exposed to domestic AC electricity, humans will get electric shocks.

Electrosurgery using high-frequency electric energy uses high-frequency electricity ranging from 200 kHz to 5 MHz.

Electric energy supplied through an electrode generates vibrations inside cells, and the temperature inside the cells increases, thereby heating the tissue.

If the temperature inside the cells reaches about 60° C., cell death occurs. If heated to 60-90° C., the tissue is dried (dehydrated), and protein coagulation proceeds. If the temperature inside the cells reaches 100° C., cells undergo volume expansion and vaporization. The tissue is incised or cauterized in such processes.

As such, electrosurgery uses high-frequency electric currents to incise and coagulate tissue. When an electrosurgical device is used to incise tissue by a high-frequency electric current, heat is generated, thereby causing a noticeable coagulation effect.

Such electrosurgical incision inevitably generates an arc at a high temperature as the air insulating layer is destroyed by incomplete contact between the conductive electrode and tissue. The arc burns tissue (burn damage). There is also a problem in that the conductive electrode is contaminated by tissue carbonization.

In addition, tissue carbonization by the arc results in smog, which is known to have adverse health influence on the surgeon and the patient.

As illustrated in FIG. 1, the monopolar electrosurgery instrument 10 has a conductive electrode 12 fastened to the front of a handpiece 11 in FIG. 2, which is held by the surgeon, and has a ground pad 15 grounded on the patient. The handpiece 11 and the ground pad 15 are connected to a control unit 13, which generates high-frequency waves, by cables, respectively.

There is a problem in that, when the conventional conductive electrode 12 is used to conduct electrosurgery, incomplete contact between the conductive electrode 12 and tissue generates a high-temperature arc, thereby resulting in tissue carbonization and smog, and the tissue adheres to the surface of the conductive electrode 12 and contaminates the same, making it necessary to frequently clean or replace the conductive electrode 12.

DISCLOSURE OF INVENTION

Technical Problem

The present disclosure has been made to solve the above-mentioned problems, and it is an aspect of the present disclosure to provide an electrosurgical handpiece conductive electrode and a method for manufacturing the same, wherein the conductive electrode is configured to have a high level of insulation and non-stickiness such that tissue carbonization and smog do not occur during an electrosurgery, and no tissue adheres to the electrode surface, which is thus not contaminated.

Solution to Problem

A method for manufacturing an electrosurgical handpiece conductive electrode according to the present disclosure includes: a blade molding step S100 of molding a blade 101 in a plate type by using aluminum as a material such that a plug 102 is provided on one side of the blade 101; an anodizing coating step S200 of anodizing the blade 101 so as to form an anodizing coating layer 104 having a thickness of 30-80 μm on a surface thereof; a primary edge portion processing step S300 of forming an edge portion 103 by removing the anodizing coating layer 104 formed on a peripheral part of the blade 101; and a non-sticky coating step S400 of forming a non-sticky coating layer 105 on the surface of the blade 101 which has undergone the anodizing coating step.

The non-sticky coating layer 105 may be formed to have a thickness of 10-40 μm by using ceramic as a material.

Alternatively, the non-sticky coating layer 105 may be formed to have a thickness of 10-30 μm by using polytetrafluoroethylene (PTFE) such as Teflon™ as a material.

In addition, the method may further include a secondary edge portion processing step S500 of removing the ceramic coating layer 105 formed on the edge portion of the blade 101 through the ceramic coating step S400.

In addition, the anodizing coating layer 104 formed in the anodizing coating step S200 may have a thickness of 40 μm, and the ceramic coating layer 105 formed in the ceramic coating step S400 may have a thickness of 30 μm.

In addition, in the primary edge portion processing step S300, a part of the anodizing coating layer 104 formed on the periphery of the blade 101 may be removed such that the edge portion 103 is formed only on a part of the periphery of the blade 101.

In addition, an electrosurgical handpiece conductive electrode according to the present disclosure is manufactured by the above-mentioned method.

Advantageous Effects of Invention

A conductive electrode according to the present disclosure, configured as described above, has an anodizing coating surface formed on a blade surface such that tissue carbonization and smog do not occur during an electrosurgery, and has a non-stick coating layer formed on the blade surface such that no tissue adheres to the blade surface, thereby enabling the surgeon to concentrate on surgery because the electrode does not need to be cleaned frequently.

BRIEF DESCRIPTION OF DRAWINGS

FIG. 1 illustrates the configuration of an electrosurgical instrument.

FIG. 2 is a perspective view of a handpiece of an electrosurgical instrument.

FIG. 3 illustrates a conductive electrode according to the present disclosure.

FIG. 4 is a sectional view of a conductive electrode according to the present disclosure, with major parts thereof magnified.

FIG. 5 is a process diagram illustrating a method for manufacturing a conductive electrode according to the present disclosure.

FIG. 6A to FIG. 6E illustrate respective processes in which a conductive electrode is processed according to the method for manufacturing a conductive electrode according to the present disclosure.

FIG. 7 illustrates a conductive electrode having an edge portion formed only on an end portion of a blade.

FIG. 8 illustrates a conductive electrode having an edge portion formed only on an upper/lower portion of a blade.

BRIEF DESCRIPTION OF MAJOR COMPONENTS IN THE DRAWINGS

10: electrosurgical instrument
11: handpiece
100: conductive electrode
101: blade
101*a*: first blade
101*b*: second blade
102: plug
103: edge portion
104: anodizing coating layer
105: non-sticky coating layer
S100: blade molding step
S200: anodizing coating step
S300: primary edge portion processing step
S400: non-sticky coating step
S500: secondary edge portion processing step

BEST MODE FOR CARRYING OUT THE INVENTION

Hereinafter, the present disclosure will be described in detail with reference to exemplary embodiments of the present disclosure and the accompanying drawings, assuming that identical reference numerals in the drawings denote identical components.

The description used in the detailed description of the present disclosure or in the claims that a component "includes" another component is to be understood as meaning that the former component may include other components, and is not to be limited to the interpretation that the same includes only the latter component, unless otherwise specified.

As used herein, terms such as "upper portion", "lower portion", "bottom", "front", "rear", and "below" are only intended to facilitate the description, and denote the orientation of components as illustrated in the drawings.

A conductive electrode 100 used for a handpiece 11 of an electrosurgical instrument incises, excises, or cauterizes tissue by using high-frequency electric energy supplied to the electrode.

The conductive electrode 100 of the present disclosure is used for a handpiece 11 of a monopolar electrosurgical instrument, and as in FIG. 2, the conductive electrode 100 is fastened to the front of the handpiece 11.

As illustrated in FIG. 3, the conductive electrode has a blade 101 formed in a plate shape, has an edge portion 103 formed on the peripheral part of the blade 101, and has a plug 102 formed behind the blade 101.

The blade 101 and the edge portion 103 are parts configured to incise or excise tissue. The plug 102 is inserted into the handpiece 11 so as to supply electric energy to the blade 101 (the role of an electric wire).

FIG. 4 is a sectional view illustrating the configuration of a blade 101 of a conductive electrode 100 according to the present disclosure.

The blade 101 of a conductive electrode 100 according to the present disclosure has an anodizing coating layer 104 and a non-stick coating layer 105 formed on the surface thereof, except for the edge portion 103.

The conductive electrode 100 according to the present disclosure is molded by using, as the material, aluminum, which has excellent conductivity and processability.

In addition, as in FIG. 4, an anodizing coating layer 104 is formed on the surface of the blade.

The anodizing coating layer 104, formed as such, plays the role of electric insulation while increasing the surface rigidity of the blade 101.

No anodizing coating layer 104 is formed on the edge portion 103 as in FIG. 4. If the anodizing coating layer 104 is formed on the edge portion 103, which emits electric energy, no surgery is possible because no electric energy is emitted.

By forming the anodizing coating layer 104 on the outer surface of the blade, except for the edge portion 103, electric energy is emitted from the edge portion 103 only such that, by increasing the current density, incision and excision are facilitated, and tissue carbonization and smog do not occur due to arc generation because no electric energy is emitted from the side surface of the blade 101.

In addition, a non-stick coating layer 105 is formed on the anodizing layer 104.

The non-stick coating layer 105 prevents tissue from adhering to the surface of the blade 101 during surgery and contaminating the blade 101.

In the case of a conventional conductive electrode, a part of tissue adheres to the surface of the blade 101 during electrosurgery and carbonizes, thereby contaminating the same. The surgeon thus needs to frequently clean the blade 101 during a surgical procedure, and the conductive electrode needs to be replaced frequently because the part that
has adhered to the blade 101 and carbonized is not easily
cleaned.

The conductive electrode 100 according to the present
disclosure has a non-stick coating layer 105 formed on the
surface of the blade 101 such that no tissue adheres to the
blade, making it unnecessary to frequently clean the blade
101 during the surgical procedure, and the electrode does not
need to be replaced until the surgery is over.

A method for manufacturing a conductive electrode
according to the present disclosure, which is configured as
described above, will now be described in detail.

A method for manufacturing a conductive electrode
according to the present disclosure includes, as illustrated in
FIG. 5, a blade molding step S100, an anodizing coating step
S200, a primary edge portion processing step S300, a
non-sticky coating step S400, and a secondary edge portion
processing step S500.

Firstly, as in FIG. 6A, aluminum is processed to mold a
plate-type blade 101 and a plug 102 on one side of the blade
101 in the blade molding step S100.

The blade 101 molded in a plate type through the blade
molding step S100 is subjected to soft anodizing such that an
anodizing coating layer 104 is formed as in FIG. 6B.

The anodizing coating layer 104 is an oxide film (alumi-
num oxide, $Al_2O_3$) which increases the surface rigidity of
surface aluminum, and which is obtained by electrolyzing
the blade 101 with a diluted acid solution across the positive
electrode, for electric insulation, such that the same is
strongly attached to the blade 101 by oxygen generated at
the positive electrode.

According to the present disclosure, the anodizing coating
layer 104 is formed on the blade 101 of the conductive
electrode 100 to have a thickness of 30-80 μm.

If the anodizing coating layer 104 has a thickness of less
than 30 μm, tissue carbonization may occur due to insuffi-
cient insulation. If the thickness of the anodizing coating
layer 104 exceeds 80 μm, cracks may occur on the coating
layer during manufacturing or circulation processes, and an
electric discharge may occur through the gaps. Therefore,
the anodizing coating layer 104 preferably has a thickness of
30-80 μm.

After the anodizing coating step S200, an edge portion is
formed on the blade 101 of the conductive electrode 100 in
a primary edge portion processing step S300.

In the primary edge portion processing step S300, the
peripheral part of the blade 101 is processed through grind-
ing or the like, as in FIG. 6C, so as to form an edge portion
103.

The anodizing coating layer 104 has electric insulation
and emits no electric energy. The peripheral part of the blade
101 is processed as in FIG. 6C to remove the anodizing
coating layer 104, thereby forming an edge portion 103 such
that electric energy is emitted through the edge portion 103,
from which the anodizing coating layer has been removed,
thereby enabling incision or excision surgery.

After the edge portion 103 is formed by processing the
peripheral part of the blade 101, the processed part is washed
clean, and a non-sticky coating layer 105 is formed on the
surface of the blade 101, as in FIG. 6D, in a non-sticky
coating step S400.

In an embodiment of the present disclosure, a ceramic
coating layer or polytetrafluoroethylene (PTFE) such as
Teflon™ coating is formed as the non-sticky coating layer
105.

When ceramic is used as the non-sticky coating layer 105,
a ceramic solution including a mixture of ceramic, dilutant, and pigment is sprayed to the surface of the blade 101 and
dried in an environment of 30-50° C. This process is
repeated multiple times, thereby forming a non-sticky coat-
ing layer 105 having a thickness of 10-40 μm.

The non-sticky coating layer 105 exhibits non-stickiness
such that tissue does not easily adhere to the surface of the
blade 101 during surgery, and tissue, even if adhered, can be
easily removed.

If the non-sticky coating layer 105 made of ceramic has
a thickness of less than 10 μm, non-stickiness and durability
are degraded. If the thickness of the non-sticky coating layer
105 exceeds 40 μm, tissue may not be incised as intended
because of insufficient electric discharge from the edge
portion. Therefore, the non-sticky coating layer 105 made of
ceramic preferably has a thickness of 10-40 μm.

On the surface of the anodizing coating layer 104 having
a thickness of 30-80 μm formed through the anodizing
coating step S200 described above, a non-sticky coating
layer 105 is formed to have a thickness of 10-40 μm by using
ceramic. Preferably, the anodizing coating layer 104 is
formed to have a thickness of 40 μm, and the non-sticky
coating layer 105 is formed to have a thickness of 30 μm to
exhibit the highest level of insulation and non-sticky per-
formance.

If polytetrafluoroethylene (PTFE) such as Teflon™ is
used as the non-sticky coating layer 105, a polytetrafluoro-
ethylene (PTFE) solution such as Teflon™ solution includ-
ing a mixture of polytetrafluoroethylene (PTFE) solution
such as Teflon™, dilutant, and pigment is sprayed to the
surface of the blade 101 and dried at a temperature of
320-400° C. This process is repeated multiple times, thereby
forming a non-sticky coating layer 105 having a thickness of
10-30 μm.

If the non-sticky coating layer 105 made of polytetrafluo-
roethylene (PTFE) such as Teflon™ has a thickness of less
than 10 μm, non-stickiness and durability are degraded. If
the thickness of the non-sticky coating layer 105 exceeds 30
μm, tissue may not be incised as intended because of
insufficient electric discharge from the edge portion. There-
fore, the non-sticky coating layer 105 made of polytetrafluo-
roethylene (PTFE) such as Teflon™ preferably has a thick-
ness of 10-30 μm.

In addition, as in FIG. 6E, the non-sticky coating layer
105 is removed from the edge portion 103 of the blade 101
in a secondary edge portion processing step S500.

The secondary edge portion processing step S500 may be
omitted, depending on conditions such as the surgery area.

In addition, in the primary edge portion processing step
S300, the peripheral part of the blade 101 may be selectively
processed, depending on conditions such as the surgery area.

As in FIG. 7, only the end periphery of the blade 101 may
be processed through grinding or the like to form an edge
portion in the primary edge portion processing step S300
such that the edge portion 103 is formed only on the end
portion of the blade 101. Alternatively, as in FIG. 8, only the
upper/lower periphery of the blade 101 may be processed
through grinding or the like to form an edge portion in the
primary edge portion processing step S300 such that the
edge portion 103 is formed only on the upper/lower portion
of the blade 101.

The conductive electrode 100 according to the present
disclosure, configured as described above, has an anodizing
coating layer 104 formed on the surface of the blade 101
such that tissue carbonization and smog do not occur during
electrosurgery, and has a non-sticky coating layer 105
formed on the blade surface such that no tissue adheres to
the blade surface, and even if a part of the tissue adheres to the side surface of the blade 101, the same can be easily wiped due to the non-sticky coating layer 105.

The technical idea of the present disclosure has been described above with reference to embodiments.

It is obvious that those skilled in the art to which the present disclosure pertains can variously modify or change the above-described embodiments in view of the description of the present disclosure.

In addition, although not explicitly illustrated or described, it is obvious that those skilled in the art to which the present disclosure pertains can make various types of modifications including the technical idea of the present disclosure in view of the description of the present disclosure, and this still falls within the scope of protection of the present disclosure.

Embodiments described above with reference to the accompanying drawings are intended to describe the present disclosure, and the scope of protection of the present disclosure is not limited by such embodiments.

The invention claimed is:

1. A method for manufacturing an electrosurgical hand-piece conductive electrode, the method comprising:

a blade molding step of molding a blade comprising aluminum in a plate shape such that a plug is provided on one side of the blade;

an anodizing coating step of anodizing the blade so as to form an anodizing coating layer having a thickness of 30-80 μm on a surface of the blade;

a primary edge portion processing step of forming an edge portion by removing the anodizing coating layer formed on a peripheral part of the blade; and a non-sticky coating step of forming a non-sticky coating layer on the surface of the blade, wherein the non-sticky coating step comprises:

preparing a ceramic solution comprising a mixture of a ceramic, a dilutant, and a pigment;

spraying the ceramic solution to the surface of the blade; and drying the ceramic solution in a temperature of 30-50° C.

2. The method of claim 1, wherein the non-sticky coating layer comprising the ceramic is formed to have a thickness of 10-40 μm.

3. The method of claim 1, further comprising a secondary edge portion processing step of removing the non-sticky coating layer formed on the edge portion of the blade through the non-sticky coating step.

4. The method of claim 2, wherein the anodizing coating layer formed in the anodizing coating step has a thickness of 40 μm, and the non-sticky coating layer comprising the ceramic material, which is formed in the non-sticky coating step has a thickness of 30 μm.

5. The method of claim 1, wherein, in the primary edge portion processing step, a part of the anodizing coating layer formed on the peripheral part of the blade is removed such that the edge portion is formed only on the part of the peripheral part of the blade.

* * * * *